United States Patent
Min et al.

(10) Patent No.: US 11,462,689 B2
(45) Date of Patent: Oct. 4, 2022

(54) ORGANIC LIGHT-EMITTING DEVICES

(71) Applicant: Kunshan Go-Visionox Opto-Electronics Co., Ltd., Kunshan (CN)

(72) Inventors: Chao Min, Kunshan (CN); Jingwen Tian, Kunshan (CN); Shengfang Liu, Kunshan (CN)

(73) Assignee: KUNSHAN GO-VISIONOX OPTO-ELECTRONICS CO., LTD., Kunshan (CN)

( * ) Notice: Subject to any disclaimer, the term of this patent is extended or adjusted under 35 U.S.C. 154(b) by 339 days.

(21) Appl. No.: 16/328,284

(22) PCT Filed: Apr. 28, 2018

(86) PCT No.: PCT/CN2018/085176
§ 371 (c)(1),
(2) Date: Feb. 26, 2019

(87) PCT Pub. No.: WO2019/041867
PCT Pub. Date: Mar. 7, 2019

(65) Prior Publication Data
US 2021/0351357 A1    Nov. 11, 2021

(30) Foreign Application Priority Data

Aug. 30, 2017   (CN) .......................... 201710763767.3

(51) Int. Cl.
*H01L 51/50* (2006.01)
*H01L 51/00* (2006.01)
(Continued)

(52) U.S. Cl.
CPC .......... *H01L 51/0059* (2013.01); *C07C 15/04* (2013.01); *C09K 11/06* (2013.01);
(Continued)

(58) Field of Classification Search
None
See application file for complete search history.

(56) References Cited

U.S. PATENT DOCUMENTS

2002/0113545 A1    8/2002   Adachi et al.
2004/0265630 A1   12/2004   Byung-Doo et al.
(Continued)

FOREIGN PATENT DOCUMENTS

CN   103915570 A    7/2014
CN   104241540 A   12/2014
(Continued)

OTHER PUBLICATIONS

EP Search Report dated Jan. 31, 2020 in the corresponding EP application (application No. 18852264.3).
(Continued)

*Primary Examiner* — Gregory D Clark
(74) *Attorney, Agent, or Firm* — Kilpatrick Townsend & Stockton

(57) ABSTRACT

The present disclosure discloses an organic light-emitting device, which includes a first electrode and a hole injection layer laminated with each other and formed an ohmic contact therebetween. The hole injection layer is characterized by a carrier mobility of less than $2\times10^{-5}$ $CM^2V^{-1}S^{-1}$.

19 Claims, 1 Drawing Sheet

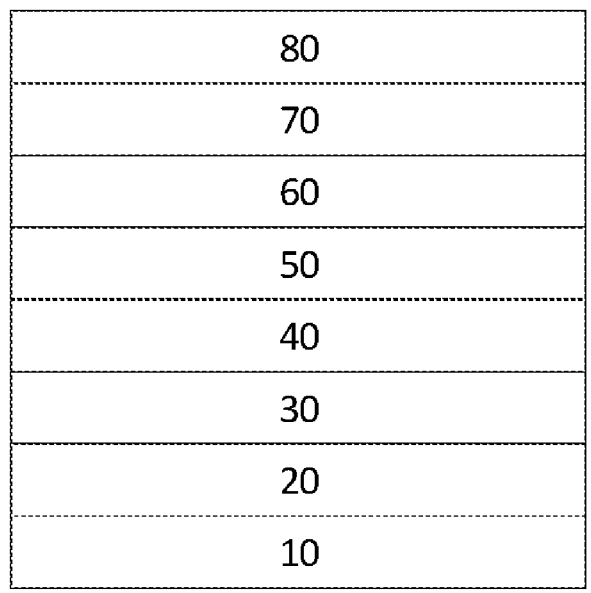

(51) Int. Cl.
*C07C 15/04* (2006.01)
*C09K 11/06* (2006.01)

(52) U.S. Cl.
CPC ...... *H01L 51/0058* (2013.01); *H01L 51/0073* (2013.01); *H01L 51/0074* (2013.01); *H01L 51/5004* (2013.01); *H01L 51/506* (2013.01)

(56) References Cited

U.S. PATENT DOCUMENTS

| | | |
|---|---|---|
| 2006/0159957 A1 | 7/2006 | Chishio et al. |
| 2009/0167159 A1 | 7/2009 | Song et al. |
| 2015/0179954 A1 | 6/2015 | Gessner et al. |
| 2016/0248030 A1 | 8/2016 | Zhang |
| 2016/0268508 A1 | 9/2016 | Kim et al. |
| 2016/0307970 A1 | 10/2016 | Kam et al. |
| 2017/0062749 A1 | 3/2017 | Seo et al. |
| 2020/0013958 A1* | 1/2020 | Suruga .................. C07C 211/61 |
| 2021/0257555 A1 | 8/2021 | Junji-Song et al. |

FOREIGN PATENT DOCUMENTS

| | | |
|---|---|---|
| CN | 106486607 A | 3/2017 |
| JP | 2010202638 A | 9/2010 |
| JP | 2016066542 | 4/2016 |
| JP | 2017120788 | 7/2017 |
| KR | 20050000747 A | 1/2005 |
| KR | 20070033947 A | 3/2007 |
| KR | 1020090072447 A | 7/2009 |
| KR | 10-2016-0122890 A | 10/2016 |
| KR | 20170067643 A | 6/2017 |
| KR | 1020170065727 A | 6/2017 |
| KR | 20170080445 A | 7/2017 |
| TW | 200609331 A | 3/2006 |
| WO | 2096006505 A1 | 1/2006 |
| WO | 2017099360 A1 | 6/2017 |

OTHER PUBLICATIONS

Office Action of KR Patent Application No. 10-2019-7021435.
TW First Office Action dated Oct. 17, 2018 in the corresponding TWapplication (application No. 107117170).
Office Action of EP Patent Application No. 18852264.3 dated Dec. 21, 2021.
Fernandes Jean Maria et al: "Investigation of hole transport in [alpha]-NPD using impedance spectroscopy with F4TCNQ as hole-injectionl", Superlattices and Microstructures, vol. 83 , pp. 766-775, XP029180051, Apr. 24, 2015. ISSN: 0749-6036, DOI: 10.1016/J.SPMI.2015.04.019.
Juhasz Peter et al.: "Charge injection and transport properties of an organic light-emitting diode", Beilstein Journal of Nanotechnology, vol. 7, Jan. 1, 2016 (Jan. 1, 2016), pp. 47-52, XP055872372, DOI: 10.3762/bjnano.7.5.
Qi-Hui Wu: "Progress in Modification of Indium-Tin Oxide/ Organic Interfaces for Organic Light-Emitting Diodes", Critical Reviews in Solid State and Materials Sciences, vol. 38, No. 4, Jan. 1, 2013 (Jan. 1, 2013), pp. 318-352, XP055481133, US ISSN: 1040-8436, DOI: 10.1080/10408436.2011.654006.
Yasuhiko Shirota and Hiroshi Kageyama: "Charge Carrier Transporting Molecular Materials and Their Applications in Devices", Chemical Reviews, American Chemical Society, US, vol. 107, No. 4, Apr. 1, 2007 (Apr. 1, 2007), pp. 953-1010, XP009141446, ISSN: 0009-2665, DOI: 10.1021 /CR050143+ [retrieved on Apr. 11, 2007].
CN First Office Action dated Aug. 1, 2019 in the corresponding CN application (application No. 201710763767.3).
Office Action of JP Patent Application No. 2019-538488 dated Jul. 14, 2020.

* cited by examiner

| 80 |
|:-:|
| 70 |
| 60 |
| 50 |
| 40 |
| 30 |
| 20 |
| 10 |

ORGANIC LIGHT-EMITTING DEVICES

CROSS-REFERENCE TO RELATED APPLICATIONS

This application is a U.S. national Stage of International Application No. PCT/CN2018/085176, filed on Apr. 28, 2018, designating the United States, which claims priority to Chinese Patent Application No. 201710763767.3, filed with the Chinese Patent Office on Aug. 30, 2017 and entitled "ORGANIC LIGHT-EMITTING DEVICE", the content of each of which is hereby incorporated by reference in its entirety.

FIELD

The present disclosure relates to the field of display technologies, and in particular, to an organic light-emitting device.

BACKGROUND

An organic light-emitting device (referred to OLED) is an active light-emitting device with advantages such as low power consumption, wide color gamut, thinner volume, and is expected to become the mainstream of the next generation of lighting and flat panel display technologies. At present, organic electroluminescence technology has been widely used in small-sized panels such as smart phone displays.

Generally, an OLED includes an anode, an organic light-emitting layer, and a cathode which are laminated on a substrate, and carrier functional layers interposed between the electrodes and the light-emitting layer. In working state, carriers (i.e., holes and electrons) are injected into the organic light-emitting layer through the anode and cathode, and different carriers are combined in the light-emitting material to release their energy in the form of light.

However, the hole mobility and electron mobility are not the same, thereby affecting the current efficiency of the OLED.

SUMMARY

Hence, a technical problem to be solved by the present disclosure is to overcome the defects of low current efficiency of the organic light-emitting device in the prior art, thereby providing an organic light-emitting device.

The present disclosure provides an organic light-emitting device comprising a first electrode and a hole injection layer which are laminated and form an ohmic contact therebetween, the hole injection layer has a carrier mobility of less than $2\times10^{-5}$ $CM^2V^{-1}S^{-1}$.

Optionally, the material constituting the hole injection layer includes a first hole transport material and a P-type doping material.

Optionally, the P-type doping material is selected from but not limited to transition metal compounds such as F4TCNQ, NDP-9 or $FeCl_3$, $MoO_3$, $WO_3$ and the like.

Optionally, the first hole transport material has a HOMO energy level within a range from −5.3 eV to −4.8 eV.

Optionally, the first hole transport material is:

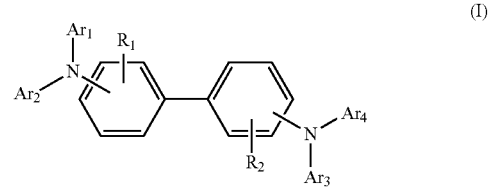

(I)

wherein, $Ar_1$ to $Ar_4$ are each independently a substituted or unsubstituted phenyl, biphenyl, terphenyl, phenanthryl; $R_1$ to $R_2$ are each independently an H atom, a $C_1$ to $C_{40}$ aliphatic straight or branched hydrocarbon group, or a halogen atom.

Optionally, the first hole transport material is selected from, but not limited to:

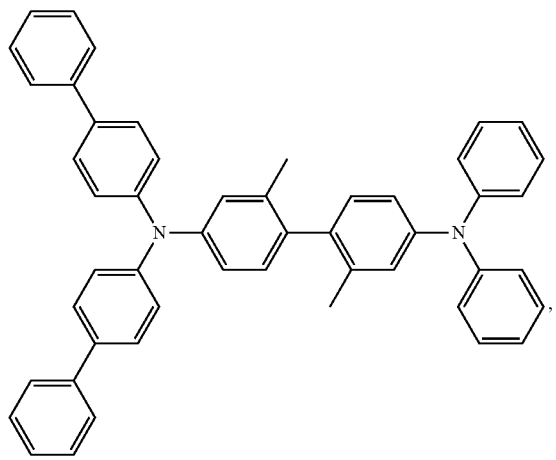

(I-1)

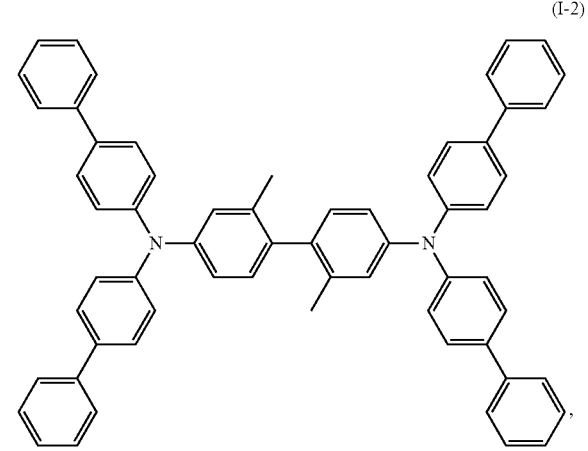

(I-2)

-continued (I-3)

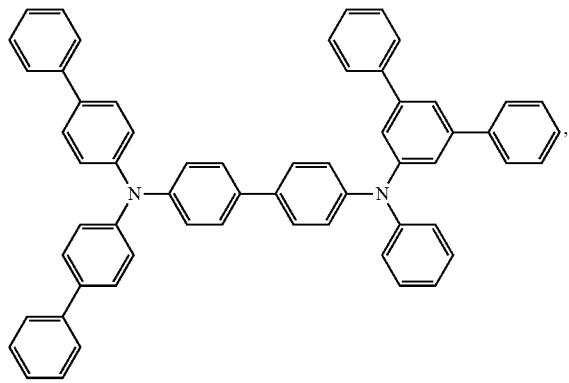

(I-4)

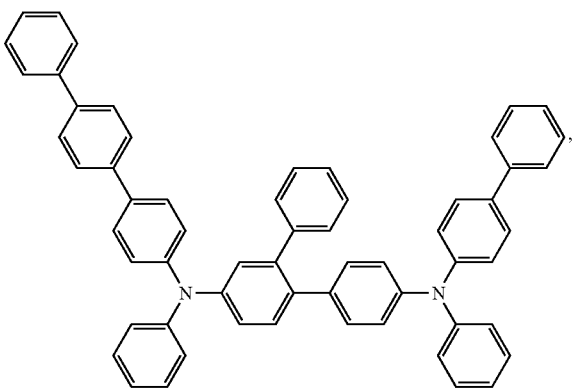

(I-5)

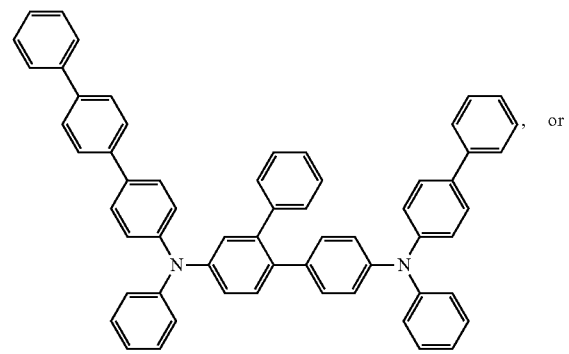, or

-continued (I-6)

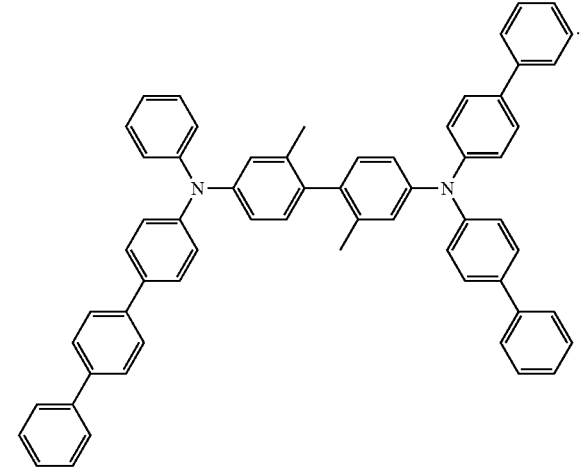

Optionally, the P-type doping material and the first hole transport material are in a mass ratio within a range from 1:100 to 1:10.

Optionally, the hole injection layer has a thickness within a range from 5 nm to 30 nm.

Optionally, the organic light-emitting device further includes a hole transport layer in ohmic contact with the hole injection layer, and a material constituting the hole transport layer is a second hole transport material, the carrier mobility of the second hole transport material is greater than that of the first hole transport material.

Optionally, the hole transport layer has a carrier mobility of greater than $1 \times 10^{-4}$ $CM^2V^{-1}S^{-1}$.

Optionally, the second hole transport material has a HOMO energy level within a range from −5.6 eV to −5.1 eV.

Optionally, the second hole transport material is:

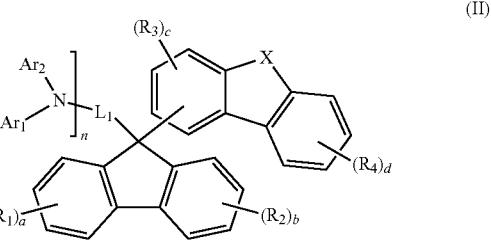

wherein, $Ar_1$ to $Ar_2$ are each independently a substituted or unsubstituted C5-C30 aromatic group;

X is O or S;

L is a single bond or an aromatic group selected from C4 to C10;

$n \geq 1$;

$R_1$ to $R_4$ are a halogen atom, a carboxyl group, or a C1 to C30 aliphatic straight or branched hydrocarbon group.

Optionally, the second hole transport material is selected from, but not limited to:

(II-1)
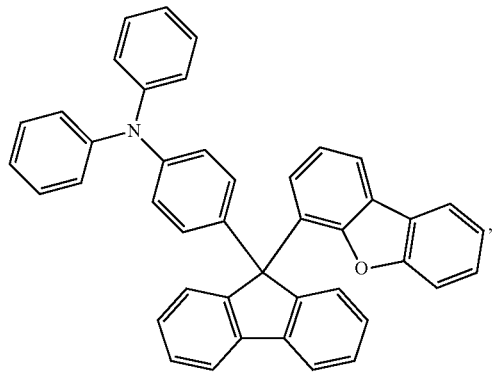

(II-2)
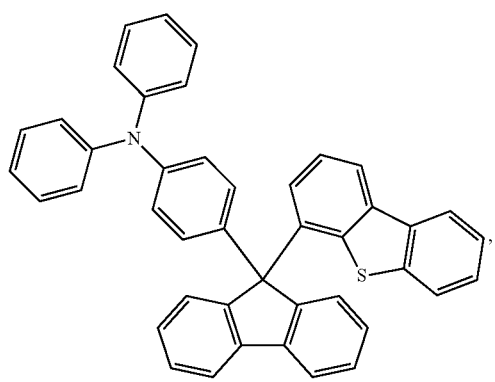

(II-3)
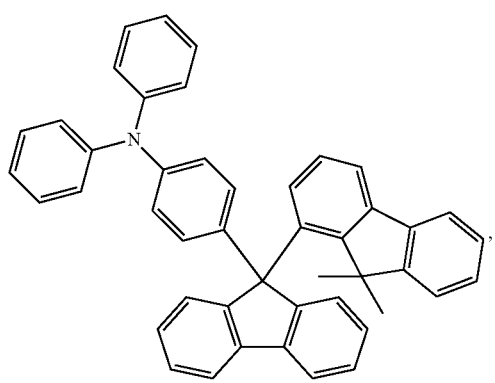

(II-4)
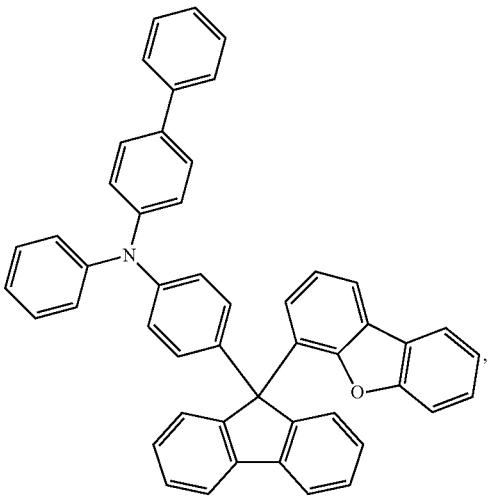

(II-5)
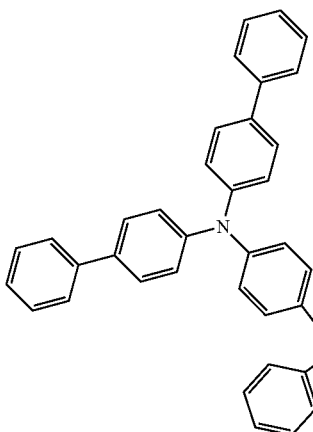

or (II-6)
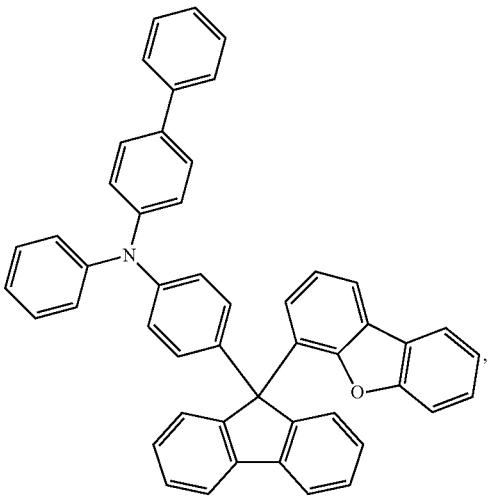

Optionally, the hole transport layer has a thickness of 50 nm to 200 nm.

The technical solution of the present disclosure has following advantages:

1. An organic light-emitting device provided in an embodiment of the present disclosure comprises a first electrode and a hole injection layer which are laminated and form an ohmic contact therebetween, wherein the hole injection layer has a carrier mobility of less than $2\times10^{-5}$ $CM^2V^{-1}S^{-1}$. The present disclosure reduces the hole mobility in the organic light-emitting device by using a material having a low mobility as a hole injection layer, thereby reducing the concentration of holes in the light-emitting layer of the OLED, so that the quantities of holes and electrons in the light-emitting layer tend to be balanced, hole-electron recombination region is increased, and then the current efficiency of the OLED is increased accordingly.

2. An organic light-emitting device is provided in an embodiment of the present disclosure, wherein the first hole transport material has a HOMO energy level of −5.3 eV to −4.8 eV. According to the present disclosure, the first hole transport material having a shallow HOMO energy level can be used as a hole injection layer, so that the hole mobility in the hole injection layer can be reduced to achieve the purpose of reducing the hole concentration in the light-emitting layer of the OLED. Moreover, there is also a P-type doping material in the material of the hole injection layer, and since the energy level overlap between the LUMO energy level of the P-type doping material and the HOMO energy level of the first hole transport material is small, the driving voltage of the OLED can be effectively reduced.

3. An organic light-emitting device is provided in an embodiment of the present disclosure, wherein the P-type doping material has a doping concentration of 1 wt. % to 10 wt. %. By using the above-mentioned doping concentration of the P-type doping material, the present disclosure is able to guarantee the quantities of holes and electrons in the light-emitting layer of the OLED tending to be balanced at the same time of reducing the hole mobility, thereby increasing the area of the hole-electron recombination region, and increasing the current efficiency of the OLED.

4. An organic light-emitting device is provided in an embodiment of the present disclosure, wherein the hole transport layer has a thickness of 50 nm to 200 nm. A microcavity structure is formed between the hole transport layer and the reflective electrode of the OLED in the present disclosure, resulting in destructive interference and constructive interference of light, and finally only maintaining the intensity of light with a predetermined wavelength and reducing the intensity of light with other wavelengths. The thickness of the hole transport layer can ensure a proper phase difference when light is reflected in the hole transport layer, thereby achieving the purpose of increasing light extraction efficiency.

BRIEF DESCRIPTION OF THE DRAWINGS

In order to more clearly illustrate the technical solutions in the specific embodiments of the present disclosure or in the prior art, the drawings used in the specific embodiments or the description of the prior art will be briefly described below, and obviously, the drawings in the following description are some embodiments of the present disclosure, and those skilled in the art can obtain other drawings based on these drawings without any creative work.

FIG. 1 is a structural schematic diagram of an OLED according to an embodiment of the present disclosure.

DETAILED DESCRIPTION OF THE INVENTION

The technical solutions of the present disclosure will be clearly and completely described in the following with reference to the accompanying drawings. It is obvious that the described embodiments are part of the embodiments of the present disclosure, and not all of the embodiments. All other embodiments obtained by those skilled in the art based on the embodiments of the present disclosure without creative work are within the scope of the present disclosure.

In the description of the present disclosure, it should be noted that although the terms "first" and "second" may be used herein to describe various features/elements, these features/elements should not be limited by these terms unless otherwise indicated. These terms may be used to distinguish one feature/element from another feature/element. Thus, the first feature/element described below may be referred to as a second feature/element, and similarly, the second feature/element discussed below may be referred to as a first feature/element without departing from the scope of the disclosure.

The present disclosure may be embodied in many different forms and should not be construed as being limited to the embodiments set forth herein. Rather, the embodiments are provided so that this disclosure will be thorough and complete, and the concept of the disclosure will be fully conveyed to those skilled in the art. The disclosure will be limited only by the claims. In the drawings, the size and relative sizes of layers and regions are exaggerated for clarity. It should be understood that when an element such as a layer is referred to as "formed on" or "disposed on" another element, the element can be disposed directly on the other element or disposed on an intermediate element that is present between the element and the other element. In contrast, when an element is referred to as being "directly formed on" or "directly disposed on" another element, no intermediate element exists.

As shown in FIG. 1, in the present embodiment, an organic light-emitting device is provided. The organic light-emitting device includes a substrate 10, and a first electrode 20, a hole injection layer 30, a hole transport layer 40, a light-emitting layer 50, an electron transport layer 60, an electron injection layer 70 and a second electrode 80, which are sequentially laminated on the substrate 10.

The substrate 10 may be a rigid substrate such as glass, or a flexible substrate sheet. Wherein, the flexible substrate sheet can be prepared by a polyester or polyimide compound material, or can be made of a thin metal sheet. The encapsulation of the organic light-emitting device can be performed by any suitable method known to those skilled in the art, such as a thin film encapsulation.

The first electrode 20 may serve as an anode and the corresponding second electrode 80 may serve as a cathode. The OLED in the embodiment of the present disclosure is described in detail by taking a top light-emitting device as an example, that is, in the present embodiment, the first electrode 20 is a transparent anode, and the second electrode 80 is a metal cathode. As an alternative embodiment of the present disclosure, the second electrode 80 is a reflective electrode.

The transparent anode 20 may be made of an inorganic material or an organic conductive polymer. The inorganic material is generally a metal oxide such as indium tin oxide (ITO), zinc oxide (ZnO) or indium zinc oxide (IZO), or a metal with a high work function, such as gold, copper or silver, wherein the ITO is preferred. The metal cathode 80 is generally made of a metal material having good conductivity such as aluminum or silver, or a conductive metal oxide. The organic conductive polymer is preferably one of polythiophene/sodium polyvinylbenzenesulfonate (hereinafter referred to as PEDOT/PSS) and polyaniline (hereinafter abbreviated as PANI).

The electron injection layer 70 may be made of a metal simple substance, or a compound formed from a metal and an oxygen group element or a halogen group element, or a metal alloy. The hole injection layer 30 and the hole transport layer 40 will be described below.

The material of the electron transport layer 60 is a fluorescent dye compound such as one of Alq, Znq, Gaq, Bebq, Bphen, Balq, DPVBi, ZnSPB, PBD, OXD, and BBOT.

The luminescent dye of the light-emitting layer 50 may be a fluorescent dye, a phosphorescent dye, or a combination thereof.

The OLED of the present disclosure may be a white light OLED or a monochrome OLED, which may be used in the field of illumination or display. In the embodiments of the present disclosure, a blue top light-emitting device is taken as an example for describing the OLED in detail.

Optionally, the hole injection layer 30 has a thickness of 5 nm to 30 nm, and the material includes a first hole transport material and a P-type doping material. The first hole transport material is represented by the formula (I) (as above), wherein $Ar_1$ to $Ar_4$ are independently a substituted or unsubstituted phenyl, biphenyl, terphenyl, phenanthrenyl; $R_1$ to $R_2$ are each independently an H atom, a $C_1$ to $C_{40}$ aliphatic straight or branched hydrocarbon group, or a halogen atom. The hole injection layer 30 has a carrier mobility of less than $2 \times 10^{-5}$ $cm^2V^{-1}S^{-1}$. The first hole transport material has a HOMO energy level of −5.3 eV to −4.8 eV.

Wherein, the P-type doping material is selected from, but not limited to, an organic dopant purchased from NOVALED Corp., for example, 2,3,5,6-tetrafluoro-7,7',8,8'-tetracyanodimethyl-p-benzoquinone (F4TCNQ), NDP-9, NDP-2, or a transition metal compound such as $FeCl_3$, $MoO_3$, $WO_3$ and the like, which has a doping concentration of 1 wt. % to 10 wt. %, preferably 3 wt. % to 5 wt. %.

In one embodiment, the hole transport layer 40 has a thickness of 50 nm to 200 nm and the material is a second hole transport material. The second hole transport material is represented by the formula (II) (as described above), wherein, $Ar_1$ to $Ar_2$ are each independently a substituted or unsubstituted C5 to C30 aromatic group; X is O or S; L is a single bond, a C4 to C10 aromatic group; $n \geq 1$; $R_1$ to $R_4$ are a halogen atom, a carboxyl group, or an C1 to C30 aliphatic straight or branched hydrocarbon group. The hole transport layer 40 has a carrier mobility of greater than $1 \times 10^{-4}$ $cm^2V^{-1}S^{-1}$, that is, the carrier mobility of the second hole transport material is greater than that of the first hole transport material. The second hole transport material has a HOMO energy level of −5.6 eV to −5.1 eV.

The materials involved in the following embodiments and comparative examples are either commercially available or laboratory synthesized.

Embodiment 1

This embodiment provides an organic light-emitting device having a structure of: ITO (20 nm)/formula (I-1): F4TCNQ (4 wt %, 20 nm)/formula (II-1) (76 nm)/AND: perylene (3 wt %, 30 nm)/Bphen (25 nm)/Ag (16 nm)/Alq3 (65 nm).

Wherein,

ITO: indium tin oxide, which is the first electrode;

AND: 9,10-bis(2-naphthyl)anthracene, which is doping material of the light-emitting layer;

Perylene: perylene, which is the main material of the light-emitting layer;

Bphen: 4,7-diphenyl-1,10-phenanthroline, which is the material of the electron transport layer;

Ag: silver, which is the second electrode;

Alq3: tris(8-hydroxyquinoline)aluminum, which is a light coupling layer.

The first hole transport material is represented by the formula (I-1), the P-type doping material is F4TCNQ, and the P-type doping material and the first hole transport material are in a mass ratio of 4:100; the hole injection layer 30 has a thickness of 20 nm; the second hole transport material is represented by the formula (II-1), and the hole transport layer 40 has a thickness of 76 nm.

In this embodiment, an ohmic contact is formed between the first electrode 20 and the hole injection layer 30, there is no significant additional impedance between the contact faces of the first electrode 20 and the hole injection layer 30, that is, a lower barrier height is existed between the contact faces, so that the holes may easily migrate from the anode 20 to the hole injection layer 30. Additionally, the hole injection layer 30 has a carrier mobility of $1.0 \times 10^{-5}$ $cm^2V^{-1}S^{-1}$. The hole mobility in the organic light-emitting device is reduced by using a material having a low mobility as a hole injection layer 30, causing that the concentration of holes in the light-emitting layer of the OLED is reduced, so that the quantities of holes and electrons in the light-emitting layer tend to be balanced, and the area of the hole-electron recombination region is increased, thereby increasing the current efficiency of the OLED.

Furthermore, the P-type doping material has a LUMO energy level of −4.9 eV, the first hole transport material has a HOMO energy level of −5.0 eV. Since the energy level overlap between the LUMO energy level of the P-type doping material and the HOMO energy level of the first hole transport material is relatively small, the driving voltage of the OLED can be effectively reduced, which increases the service life of the OLED.

In this embodiment, the P-type doping material has a doping concentration of 4%, and the hole injection layer doped at this concentration is capable to guarantee the quantities of holes and electrons in the light-emitting layer of the OLED to be balanced while reducing the hole mobility, thereby increasing the area of the hole-electron recombination region, and increasing the current efficiency of the OLED.

Wherein, the hole transport layer 30 has a thickness of 20 nm, and the hole injection layer 30 with the thickness can increase the current efficiency of the OLED on one hand, and can stabilize the working voltage of the OLED on the other hand, thereby increasing the service life of the OLED.

In the present embodiment, the hole transport layer 40 has a carrier mobility of $2.8 \times 10^{-4}$ $cm^2V^{-1}S^{-1}$, and a hole mobility of $3 \times 10^{-4}$ $cm^2V^{-1}S^{-1}$, that is, the carrier mobility of the hole transport layer 40 is substantially equal to the hole mobility, which is able to ensure effective injections of holes, thereby increasing the probability of recombination of holes and electrons in the light-emitting layer 50.

In this embodiment, a first hole transport material has a HOMO energy level of −5.0 eV. By selecting a material having a shallow HOMO energy level as the first hole transport material in hole injection layer 30, the hole mobility in the hole injection layer can be reduced to achieve the purpose of reducing the hole concentration in the light-emitting layer of the OLED. Moreover, the second hole transport material has a HOMO energy level of −5.4 eV. Since the second hole transport material has a lower HOMO energy level than that of the first hole transport material, the hole mobility of the hole injection layer 30 is reduced, which reduces the concentration of holes in the light-emitting layer 50 of OLED, increases the area of the hole-electron recombination region in the light-emitting layer 50, and effectively increases the current efficiency of the OLED.

In this embodiment, the hole transport layer 40 and the reflective electrode 80 of the OLED form a microcavity structure, that results in destructive interference and constructive interference of light, and finally only the intensity of light with a predetermined wavelength is maintained and the intensity of light with other wavelengths is reduced.

As an optionally implemental mode of this embodiment, when the microcavity structure is adjusted, the transmittance of the light may be controlled by adjusting the thickness of the hole transport layer 40, thereby adjusting the phase difference generated when light is reflected in the hole transport layer 40.

As an alternative embodiment of the present disclosure, any of the organic light emitting diodes in the prior art, which has a hole injection layer structure conforming to the scope of the claims of the present disclosure, can be used for the purpose of the present disclosure and fall within the scope of the present disclosure.

Embodiment 2

This embodiment provides an organic light-emitting device having the same structure as that in Embodiment 1, except that the first hole transport material is represented by the formula (I-1), the P-type doping material is F4TCNQ, the hole injection layer 30 has a thickness of 10 nm, and the P-type doping material has a doping concentration of 8%; and the second hole transport material is represented by the formula (II-2), and the hole transport layer 40 has a thickness of 86 nm.

Embodiment 3

This embodiment provides an organic light-emitting device having the same structure as that in Embodiment 1, except that the first hole transport material is represented by the formula (I-2), the P-type doping material is F4TCNQ, the hole injection layer 30 has a thickness of 10 nm, and the P-type doping material has a doping concentration of 4%; and the second hole transport material is represented by the formula (II-3), and the hole transport layer 40 has a thickness of 86 nm.

Embodiment 4

This embodiment provides an organic light-emitting device having the same structure as that in Embodiment 1, except that the first hole transport material is represented by the formula (I-3), the P-type doping material is F4TCNQ, the hole injection layer 30 has a thickness of 8 nm, and the P-type doping material has a doping concentration of 4%; and the second hole transport material is represented by the formula (II-3), and the hole transport layer 40 has a thickness of 88 nm.

Embodiment 5

This embodiment provides an organic light-emitting device having the same structure as that in Embodiment 1, except that the first hole transport material is represented by the formula (I-4), the P-type doping material is F4TCNQ, the hole injection layer 30 has a thickness of 7 nm, and the P-type doping material has a doping concentration of 4%; and the second hole transport material is represented by the formula (II-4), and the hole transport layer 40 has a thickness of 89 nm.

Embodiment 6

This embodiment provides an organic light-emitting device having the same structure as that in Embodiment 1, except that the first hole transport material is represented by the formula (I-4), the P-type doping material is NDP-9, the hole injection layer 30 has a thickness of 6 nm, and the P-type doping material has a doping concentration of 4%; and the second hole transport material is represented by the formula (II-5), and the hole transport layer 40 has a thickness of 90 nm.

Embodiment 7

This embodiment provides an organic light-emitting device having the same structure as that in Embodiment 1, except that the first hole transport material is represented by the formula (I-5), the P-type doping material is NDP-9, the hole injection layer 30 has a thickness of 10 nm, and the P-type doping material has a doping concentration of 2%; and the second hole transport material is represented by the formula (II-6), and the hole transport layer 40 has a thickness of 86 nm.

Embodiment 8

This embodiment provides an organic light-emitting device having the same structure as that in Embodiment 1, except that the first hole transport material is represented by the formula (I-5), the P-type doping material is NDP-9, the hole injection layer 30 has a thickness of 10 nm, and the P-type doping material has a doping concentration of 1%; and the second hole transport material is represented by the formula (II-1), and the hole transport layer 40 has a thickness of 86 nm.

Embodiment 9

This embodiment provides an organic light-emitting device having the same structure as that in Embodiment 1, except that the first hole transport material is represented by the formula (I-6), the P-type doping material is NDP-9, the hole injection layer 30 has a thickness of 5 nm, and the P-type doping material has a doping concentration of 4%; and the second hole transport material is represented by the formula (II-1), and the hole transport layer 40 has a thickness of 100 nm.

Embodiment 10

This embodiment provides an organic light-emitting device having the same structure as that in Embodiment 1, except that the first hole transport material is represented by the formula (I-6), the P-type doping material is F4TCNQ, the hole injection layer 30 has a thickness of 25 nm, and the P-type doping material has a doping concentration of 4%; and the second hole transport material is represented by the formula (II-2), and the hole transport layer 40 has a thickness of 120 nm.

Embodiment 11

This embodiment provides an organic light-emitting device having the same structure as that in Embodiment 1, except that the first hole transport material is represented by the formula (I-1), the P-type doping material is F4TCNQ, the hole injection layer 30 has a thickness of 30 nm, and the P-type doping material has a doping concentration of 4%; and the second hole transport material is represented by the formula (II-6), and the hole transport layer 40 has a thickness of 200 nm.

Embodiment 12

This embodiment provides an organic light-emitting device having the same structure as that in Embodiment 1, except that the first hole transport material is represented by the formula (I-1), the P-type doping material is F4TCNQ, the hole injection layer 30 has a thickness of 10 nm, and the P-type doping material has a doping concentration of 3%; and the second hole transport material is represented by the formula (II-5), and the hole transport layer 40 has a thickness of 86 nm.

Embodiment 13

This embodiment provides an organic light-emitting device having the same structure as that in Embodiment 1, except that the first hole transport material is represented by the formula (I-2), the P-type doping material is NDP-9, the hole injection layer 30 has a thickness of 10 nm, and the P-type doping material has a doping concentration of 5%; and the second hole transport material is represented by the formula (II-5), and the hole transport layer 40 has a thickness of 86 nm.

Embodiment 14

This embodiment provides an organic light-emitting device having the same structure as that in Embodiment 1, except that the first hole transport material is represented by the formula (I-2), the P-type doping material is NDP-9, the hole injection layer 30 has a thickness of 10 nm, and the P-type doping material has a doping concentration of 10%; and the second hole transport material is represented by the formula (II-4), and the hole transport layer 40 has a thickness of 86 nm.

Embodiment 15

This embodiment provides an organic light-emitting device having the same structure as that in Embodiment 1, except that the first hole transport material is represented by the formula (I-3), the P-type doping material is NDP-9, the hole injection layer 30 has a thickness of 12 nm, and the P-type doping material has a doping concentration of 3%; and the second hole transport material is represented by the formula (II-5), and the hole transport layer 40 has a thickness of 65 nm.

Embodiment 16

This embodiment provides an organic light-emitting device having the same structure as that in Embodiment 1, except that the first hole transport material is represented by the formula (I-2), the P-type doping material is F4TCNQ, the hole injection layer 30 has a thickness of 11 nm, and the P-type doping material has a doping concentration of 10%; and the second hole transport material is represented by the formula (II-5), and the hole transport layer 40 has a thickness of 50 nm.

Comparative Example 1

This comparative example provides an organic light-emitting device, including: a substrate, and a first electrode, a hole injection layer, a hole transport layer, a light-emitting layer, an electron transport layer, an electron injection layer, and a second electrode which are sequentially laminated on the substrate. The specific structure is the same as that of Embodiment 1, except that the first hole transport material is represented by the formula (I-1), the hole injection layer has a thickness of 40 nm, and the P-type doping material has a doping concentration of 4%; and the second hole transport material is represented by the formula (II-5), and the hole transport layer has a thickness of 100 nm.

Comparative Example 2

This comparative example provides an organic light-emitting device having the same structure as that in Embodiment 1, except that the first hole transport material is represented by the formula (I-2), the hole injection layer has a thickness of 10 nm, and the P-type doping material has a doping concentration of 0.5%; and the second hole transport material is represented by the formula (II-1), and the hole transport layer 40 has a thickness of 86 nm.

Comparative Example 3

This comparative example provides an organic light-emitting device having the same structure as that in Embodiment 1, except that the hole injection layer has a thickness of 0 nm, and the P-type doping material has a doping concentration of 0%; and the second hole transport material is represented by the formula (II-2), and the hole transport layer 40 has a thickness of 90 nm.

Comparative Example 4

This comparative example provides an organic light-emitting device having the same structure as that in Embodiment 1, except that the first hole transport material is represented by the formula (I-4), the hole injection layer has a thickness of 10 nm, and the P-type doping material has a doping concentration of 0%; and the second hole transport material is represented by the formula (II-3), and the hole transport layer has a thickness of 76 nm.

Comparative Example 5

This comparative example provides an organic light-emitting device having the same structure as that in Embodiment 1, except that the first hole transport material is represented by the formula (I-5), the P-type doping material is NDP-9, the hole injection layer has a thickness of 12 nm, and the P-type doping material has a doping concentration of 3%; and the second hole transport material is represented by the formula (II-1), and the hole transport layer 40 has a thickness of 0 nm.

Comparative Example 6

This comparative example provides an organic light-emitting device having the same structure as that in Embodiment 1, except that the first hole transport material is represented by the formula (II-6), the P-type doping material is NDP-9, the hole injection layer has a thickness of 10 nm, and the P-type doping material has a doping concentration of 4%; and the second hole transport material is represented by the formula (II-6), and the hole transport layer 40 has a thickness of 86 nm.

TABLE 1

The specific structure of the organic light-emitting device corresponding to each of the embodiments and comparative examples

|  | Hole injection layer | | Hole transport layer Thickness (nm) |
|---|---|---|---|
|  | Thickness (nm) | Doping concentration of P-type doping material (wt %) | |
| Embodiment 1 | 20 | 4 | 76 |
| Embodiment 2 | 10 | 8 | 86 |
| Embodiment 3 | 10 | 4 | 86 |
| Embodiment 4 | 8 | 4 | 88 |
| Embodiment 5 | 7 | 4 | 89 |
| Embodiment 6 | 6 | 4 | 90 |
| Embodiment 7 | 10 | 2 | 86 |
| Embodiment 8 | 10 | 1 | 86 |
| Embodiment 9 | 5 | 4 | 100 |
| Embodiment 10 | 25 | 4 | 120 |
| Embodiment 11 | 30 | 4 | 200 |
| Embodiment 12 | 10 | 3 | 86 |
| Embodiment 13 | 10 | 5 | 86 |
| Embodiment 14 | 10 | 10 | 86 |
| Embodiment 15 | 12 | 3 | 65 |
| Embodiment 16 | 11 | 10 | 50 |
| Comparative example 1 | 40 | 4 | 100 |
| Comparative example 2 | 10 | 0.5 | 86 |
| Comparative example 3 | 0 | 0 | 90 |
| Comparative example 4 | 10 | 0 | 76 |
| Comparative example 5 | 12 | 3 | 0 |
| Comparative example 6 | 10 | 4 | 86 |

TABLE 2

Table of parameter test of organic light-emitting device corresponding to each of the embodiments and comparative examples

|  | Driving voltage (V) | Current efficiency (cd/A) |
|---|---|---|
| Embodiment 1 | 4.25 | 5.88 |
| Embodiment 2 | 4.28 | 5.91 |
| Embodiment 3 | 4.28 | 6.21 |
| Embodiment 4 | 4.43 | 6.42 |
| Embodiment 5 | 4.46 | 6.82 |
| Embodiment 6 | 4.6 | 6.33 |
| Embodiment 7 | 4.41 | 6.38 |
| Embodiment 8 | 4.91 | 6.59 |
| Embodiment 9 | 4.63 | 6.34 |
| Embodiment 10 | 4.23 | 5.83 |
| Embodiment 11 | 4.05 | 5.79 |
| Embodiment 12 | 4.28 | 6.80 |
| Embodiment 13 | 4.29 | 5.82 |
| Embodiment 14 | 4.29 | 5.87 |
| Embodiment 15 | 4.29 | 5.89 |
| Embodiment 16 | 4.28 | 5.86 |
| Comparative example 1 | 5.10 | 5.76 |
| Comparative example 2 | 4.28 | 5.78 |
| Comparative example 3 | 5.23 | 5.73 |
| Comparative example 4 | 4.28 | 5.72 |
| Comparative example 5 | 4.29 | 5.70 |
| Comparative example 6 | 4.38 | 5.62 |

Comparing the data of Embodiment 1 and Comparative Example 6 in the above Tables 1 and 2, it can be seen that the current efficiency in Embodiment 1 is 10% higher than that in Comparative Example 6; that means, selecting a first hole transport material having a low mobility as the hole injection layer, so as to reduce the hole mobility in the OLED, then reduce the concentration of holes in the light-emitting layer of the OLED, balance the quantities of holes and electrons in the light-emitting layer, increase the area of the hole-electron recombination region that is beneficial to the balance of electrons and holes, and thereby effectively improve the current efficiency of the OLED. By comparing Embodiment 1, 3 to 6, 9 to 11 and Comparative Example 1 in Tables 1 and 2, it can be seen from the data therein that when the thickness of the hole injection layer is reduced, the current efficiency of the corresponding OLED is increased, and the voltage of the OLED is stable when the thickness of the hole injection layer exceeds 10 nm. By comparing Embodiment 2, 3, 7, 8, 12 to 16 and Comparative Example 2, it can be seen from the data therein that when the doping concentration of the P-type doping material is reduced, the current efficiency of the OLED is increased, and when the doping concentration exceeds 4 wt %, the band bending of injection barrier tends to be saturated, and the voltage of the corresponding OLED is stable. Therefore, as shown in Comparative Examples 3 to 5, the object of the present disclosure could not be achieved when either of the hole injection layer and the hole transport layer is not provided, or the P-type doping is not present in the hole injection layer.

It is apparent that the above-described embodiments are merely illustrative of the examples, and are not intended to limit the embodiments. Other variations or modifications in various forms may be made by those skilled in the art in light of the above description. There is no need and no way to exhaust all of the embodiments. Obvious changes or variations resulting therefrom are still within the scope of the disclosure.

The invention claimed is:

1. An organic light-emitting device, comprising a first electrode and a hole injection layer which are laminated and form an ohmic contact therebetween, the hole injection layer comprises a first hole transport material;
   a carrier mobility of the hole injection layer being less than $2 \times 10^{-5} CM^2 V_{-1} S^{-1}$; and
   a hole transport layer in ohmic contact with the hole injection layer, the hole transport layer comprising a second hole transport material characterized by a carrier mobility greater than that of the first hole transport material.

2. The organic light-emitting device according to claim 1, wherein the hole injection layer further comprises a P-type doping material.

3. The organic light-emitting device according to claim 2, wherein the P-type doping material is selected from one or more of F4TCNQ, NDP-9, $FeCl_3$, $MoO_3$, and $WO_3$.

4. The organic light-emitting device according to claim 2, wherein the first hole transport material is characterized by a HOMO energy level of −5.3 eV to −4.8 eV.

5. The organic light-emitting device according to claim 2, wherein the first hole transport material is:

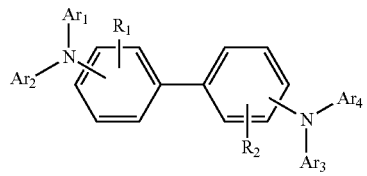
(I)

Ar$_1$ to Ar$_4$ representing a substituted or unsubstituted phenyl, biphenyl, terphenyl, or phenanthryl, respectively;

R$_1$ to R$_2$ representing an H atom, a C$_1$ to C$_{40}$ aliphatic straight or branched hydrocarbon group, or a halogen atom, respectively.

6. The organic light-emitting device according to claim 5, wherein the first hole transport material is:

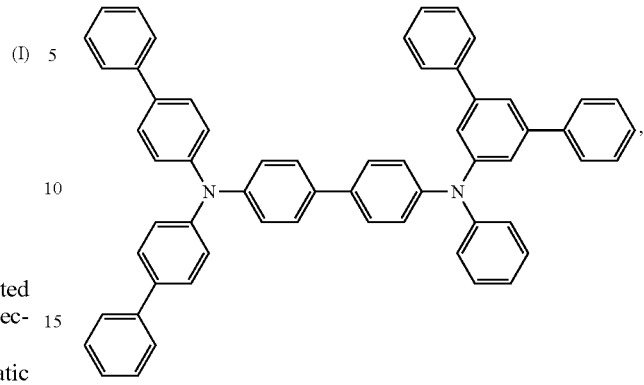
(I-3)

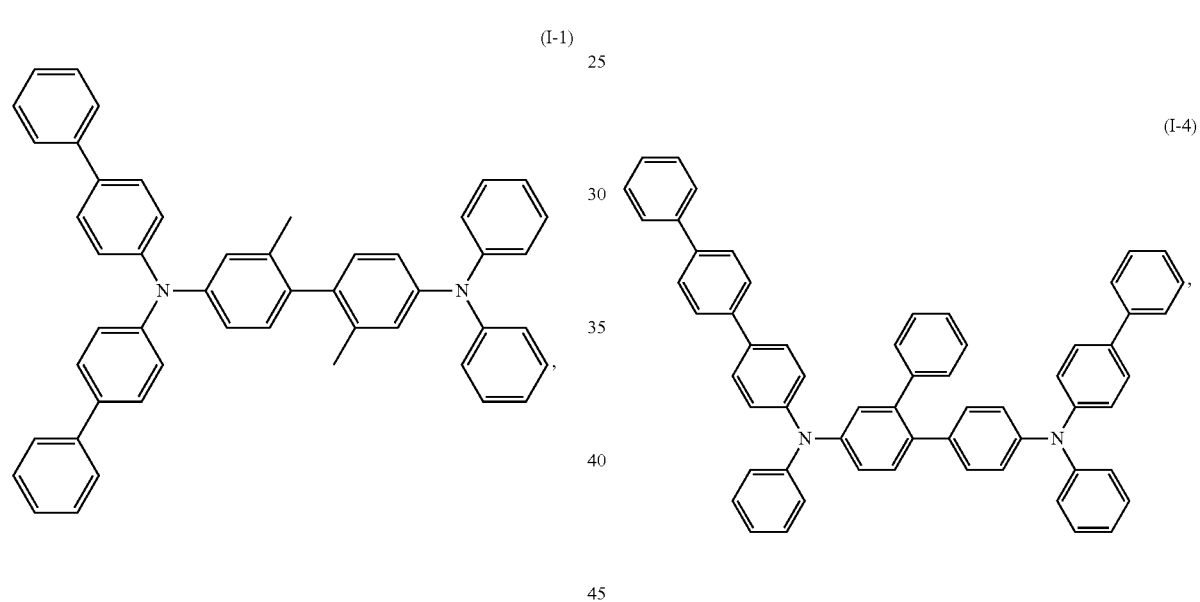
(I-1)

(I-2)

(I-4)

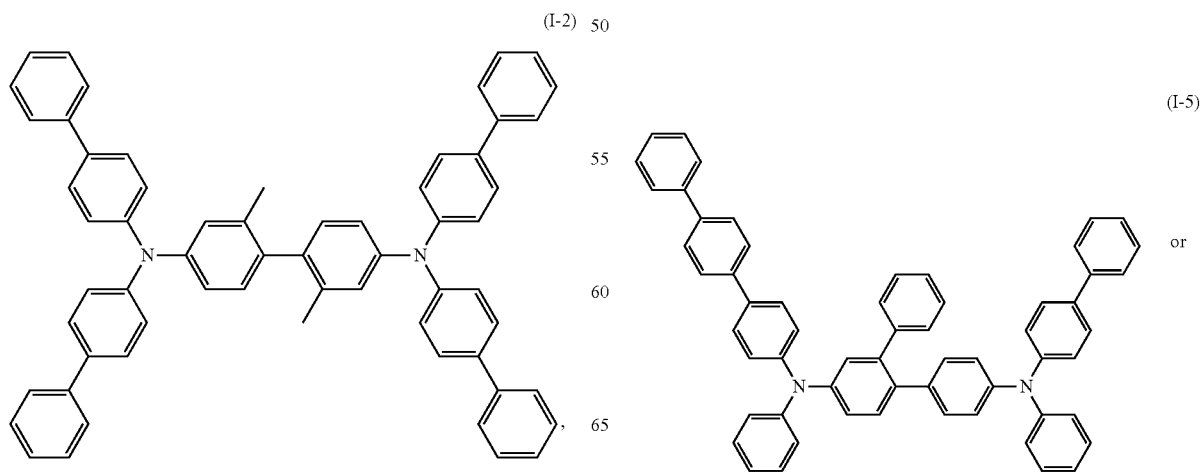
(I-5)

or

-continued (I-6)

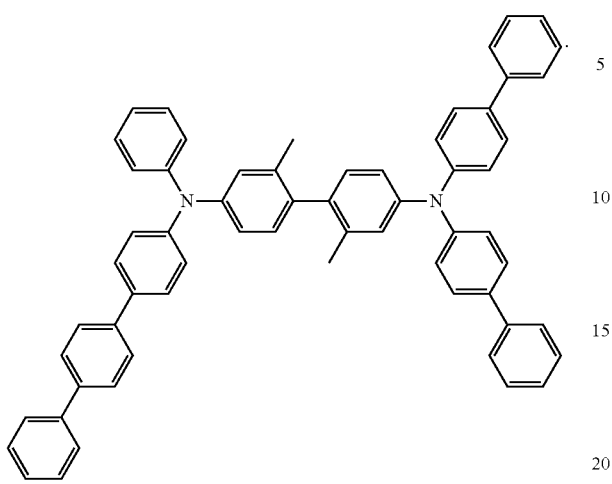

7. The organic light-emitting device according to claim 2, wherein a mass ratio of the P-type doping material to the first hole transport material is between 1:100 to 1:10.

8. The organic light-emitting device according to claim 1, wherein the hole injection layer is characterized by a thickness from 5 nm to 30 nm.

9. The organic light-emitting device according to claim 1, wherein the hole transport layer is characterized by a carrier mobility greater than $1 \times 10^{-4}$ $CM^2V^{-1}S^{-1}$.

10. The organic light-emitting device according to claim 1, wherein the second hole transport material is characterized by a HOMO energy level between −5.6 eV to −5.1 eV.

11. The organic light-emitting device according to claim 1, wherein the second hole transport material is:

(II)

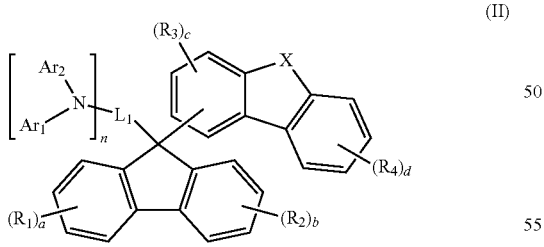

Ar$_1$ and Ar$_2$ respectively representing a substituted or unsubstituted C5-C30 aromatic group;

X representing O or S;

L representing a single bond or a C4 to C10 aromatic group;

n≥1;

R$_1$ to R$_4$ respectively representing a halogen atom, a carboxyl group, or a C1 to C30 aliphatic straight or branched hydrocarbon group.

12. The organic light-emitting device according to claim 11, wherein the second hole transport material includes:

(II-1)

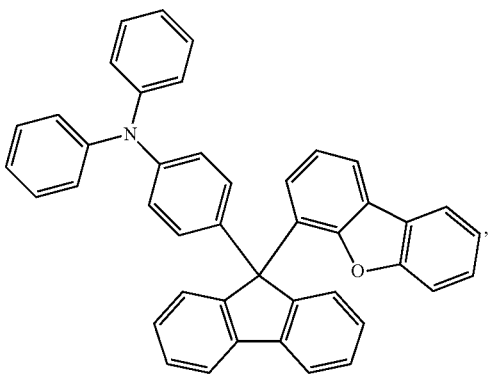

(II-2)

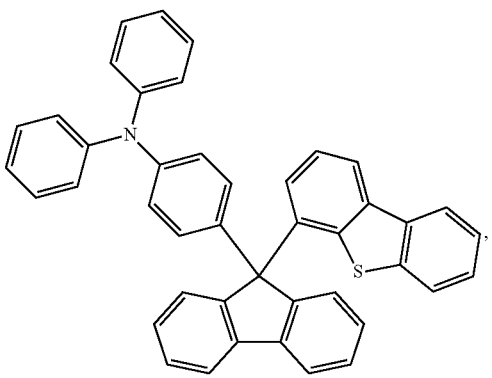

(II-3)

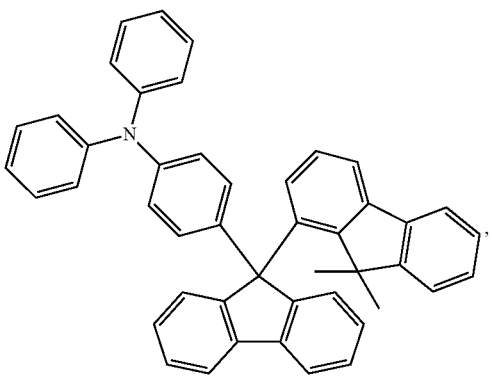

-continued (II-4)

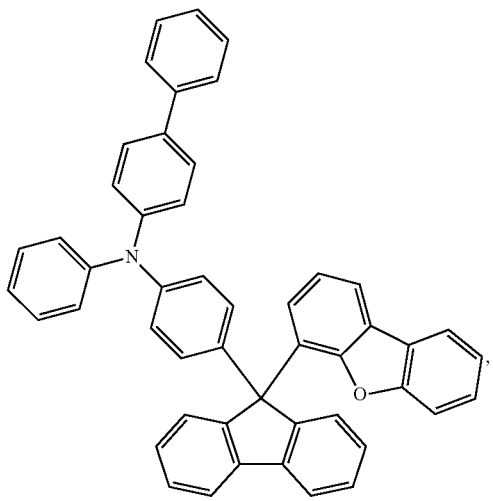

(II-5)

(II-6)

13. The organic light-emitting device according to claim 1, wherein the hole transport layer is characterized by a thickness between 50 nm to 200 nm.

14. An organic light-emitting device, comprising:

a first electrode and a hole injection layer which are laminated and form an ohmic contact therebetween; and a carrier mobility of the hole injection layer being less than $2 \times 10^{-5} CM^2V^{-1}S^{-1}$;

wherein the hole injection layer comprises a first hole transport material selected from the group consisting of:

(I-1)

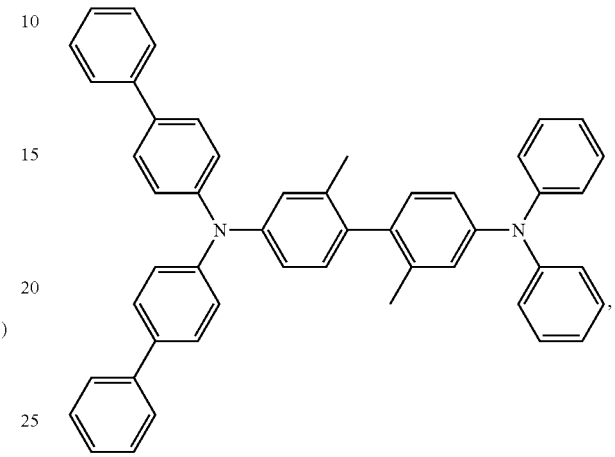

(I-2)

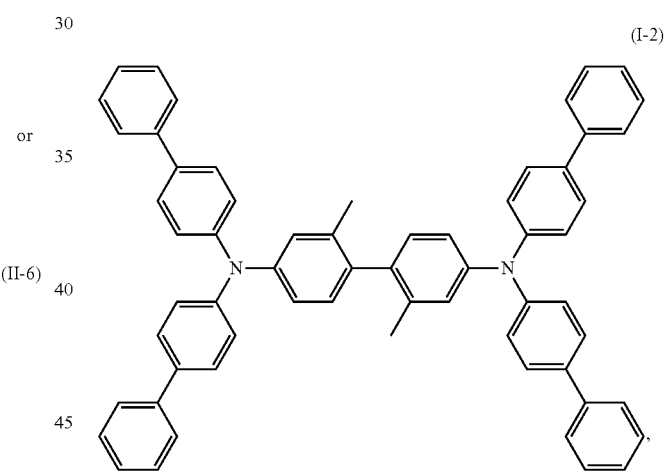

(I-3)

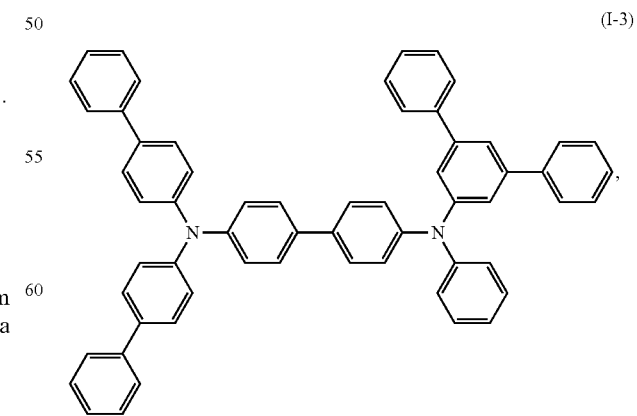

and (I-6)

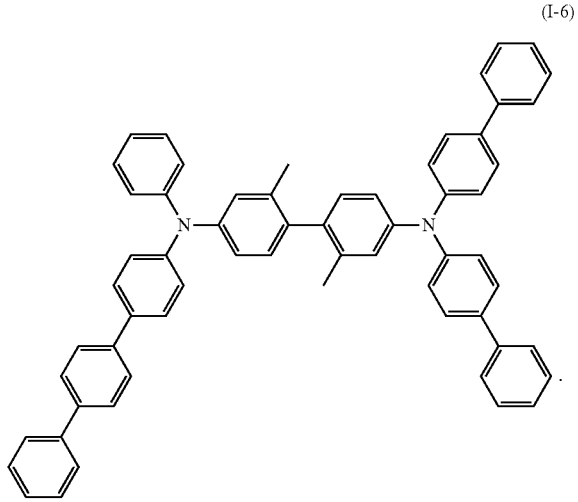

15. The organic light-emitting device according to claim 14, wherein the hole injection layer further comprises a P-type doping material.

16. The organic light-emitting device according to claim 15, wherein the P-type doping material is selected from one or more of F4TCNQ, NDP-9, FeCl3, MoO3, and WO3.

17. The organic light-emitting device according to claim 14, further comprising a hole transport layer in ohmic contact with the hole injection layer, the hole transport layer is consisted of a second hole transport material characterized by a carrier mobility greater than that of the first hole transport material.

18. The organic light-emitting device according to claim 17, wherein the hole transport layer is characterized by a carrier mobility greater than 1×10-4 CM2V-1S-1.

19. The organic light-emitting device according to claim 17, wherein the second hole transport material is characterized by a HOMO energy level between −5.6 eV to −5.1 eV.

* * * * *